(12) United States Patent
Zampini et al.

(10) Patent No.: US 8,501,383 B2
(45) Date of Patent: *Aug. 6, 2013

(54) COATING COMPOSITIONS FOR USE WITH AN OVERCOATED PHOTORESIST

(75) Inventors: Anthony Zampini, Westborough, MA (US); Vipul Jain, Westborough, MA (US); Cong Liu, Shrewsbury, MA (US); Suzanne Coley, Mansfield, MA (US); Owendi Ongayi, Marlborough, MA (US)

(73) Assignee: Rohm and Haas Electronic Materials LLC, Marlborough, MA (US)

( * ) Notice: Subject to any disclaimer, the term of this patent is extended or adjusted under 35 U.S.C. 154(b) by 45 days.

This patent is subject to a terminal disclaimer.

(21) Appl. No.: 12/782,350

(22) Filed: May 18, 2010

(65) Prior Publication Data

US 2011/0033800 A1 Feb. 10, 2011

Related U.S. Application Data

(60) Provisional application No. 61/216,795, filed on May 20, 2009.

(51) Int. Cl.
*G03F 7/004* (2006.01)
*C07D 251/34* (2006.01)
*C08G 73/08* (2006.01)

(52) U.S. Cl.
USPC ............... 430/270.1; 430/271.1; 430/927; 528/367; 528/289

(58) Field of Classification Search
USPC .................. 430/270.1, 271.1, 927
See application file for complete search history.

(56) References Cited

U.S. PATENT DOCUMENTS

| 7,423,599 | B2* | 9/2008 | Li et al. | 343/702 |
| 7,794,919 | B2* | 9/2010 | Kishioka | 430/311 |
| 8,021,826 | B2* | 9/2011 | Kim et al. | 430/271.1 |
| 2006/0234156 | A1* | 10/2006 | Kishioka | 430/270.1 |
| 2010/0009293 | A1* | 1/2010 | Yao et al. | 430/312 |
| 2010/0009297 | A1* | 1/2010 | Yao et al. | 430/325 |
| 2010/0092894 | A1* | 4/2010 | Liu et al. | 430/325 |
| 2011/0200938 | A1* | 8/2011 | Yao et al. | 430/280.1 |
| 2011/0250544 | A1* | 10/2011 | Liu et al. | 430/325 |

FOREIGN PATENT DOCUMENTS

| EP | 1560070 A1 * | 8/2005 |
| WO | WO 2004090640 A1 * | 10/2004 |

* cited by examiner

*Primary Examiner* — Amanda C. Walke
(74) *Attorney, Agent, or Firm* — Peter F. Corless; Darryl P. Frickey; Edwards Wildman Palmer LLP

(57) ABSTRACT

Cyanurate compositions are provided that are particularly useful as a reagent to form a resin component of a coating composition underlying an overcoated photoresist. Preferred isocyanurates compound comprise substitution of multiple cyanurate nitrogen ring atoms by at least two distinct carboxy and/or carboxy ester groups.

10 Claims, No Drawings

COATING COMPOSITIONS FOR USE WITH AN OVERCOATED PHOTORESIST

This application claims the benefit of priority under 35 U.S.C. §119(e) to U.S. Provisional Application No. 61/216,795, filed May 20, 2009, the contents of which application are incorporated herein by reference.

The present invention relates to cyanurate compositions that are particularly useful as a reagent to form a resin component of a coating composition underlying an overcoated photoresist.

Photoresists are photosensitive films used for the transfer of images to a substrate. A coating layer of a photoresist is formed on a substrate and the photoresist layer is then exposed through a photomask to a source of activating radiation. The photomask has areas that are opaque to activating radiation and other areas that are transparent to activating radiation. Exposure to activating radiation provides a photo-induced or chemical transformation of the photoresist coating to thereby transfer the pattern of the photomask to the photoresist-coated substrate. Following exposure, the photoresist is developed to provide a relief image that permits selective processing of a substrate.

A major use of photoresists is in semiconductor manufacture where an object is to convert a highly polished semiconductor slice, such as silicon or gallium arsenide, into a complex matrix of electron conducting paths that perform circuit functions. Proper photoresist processing is a key to attaining this object. While there is a strong interdependency among the various photoresist processing steps, exposure is believed to be one of the most important steps in attaining high resolution photoresist images.

Reflection of activating radiation used to expose a photoresist often poses limits on resolution of the image patterned in the photoresist layer. Reflection of radiation from the substrate/photoresist interface can produce spatial variations in the radiation intensity in the photoresist, resulting in non-uniform photoresist linewidth upon development. Radiation also can scatter from the substrate/photoresist interface into regions of the photoresist where exposure is non-intended, again resulting in linewidth variations.

One approach used to reduce the problem of reflected radiation has been the use of a radiation absorbing layer interposed between the substrate surface and the photoresist coating layer. See U.S. Pat. No. 7,425,403.

Electronic device manufacturers continually seek increased resolution of a photoresist image patterned over antireflective coating layers.

In one aspect, we provide new cyanurate-type monomers that are useful to form resins of distinct underlying antireflective coating compositions.

In a further aspect, resins are provided that comprise a reacted cyanurate-type monomer as disclosed herein.

In a preferred aspect, cyanurate-type compounds are provided that comprise substitution of multiple cyanurate nitrogen ring atoms by distinct (different) carboxy (e.g. —COOH) and/or carboxy ester (e.g. COOR where R is other than hydrogen such as $C_{1-12}$alkyl) substitution. In this aspect, particularly preferred compounds include those of the following Formula I:

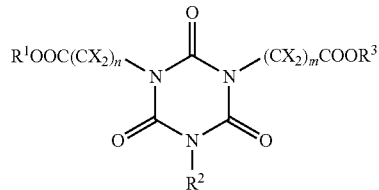

I wherein at least two of the radicals $R^1OOC(CX_2)_n-$, $R^2-$ and $R^3OOC(CX_2)_m-$ are different acid or ester groups; and $R^1$, $R^2$, $R^3$ and each X are each independently hydrogen or non-hydrogen substituent such as optionally substituted alkyl (e.g. optionally substituted $C_{1-10}$ alkyl), optionally substituted alkenyl or alkynyl preferably having 2 to about 10 carbon atoms such as such as allyl, optionally substituted alkanoyl preferably having 1 to about 10 carbon atoms; optionally substituted alkoxy (including epoxy) preferably having 1 to about 10 carbon atoms such as methoxy, propoxy, butoxy; optionally substituted alkylthio preferably having 1 to about 10 carbon atoms; optionally substituted alkylsulfinyl preferably 1 to about 10 carbon atoms; optionally substituted alkylsulfonyl preferably having 1 to about 10 carbon atoms; optionally substituted carboxy preferably have 1 to about 10 carbon atoms (which includes groups such as —COOR' where R' is H or $C_{1-8}$alkyl, including esters that are substantially non-reactive with photoacid); optionally substituted alkaryl such as optionally substituted benzyl, optionally substituted carbocyclic aryl such as optionally substituted phenyl, naphthyl, acenaphthyl, or optionally substituted heteralicyclic or heteroaromatic group such as methylphthalimide, N-methyl-1,8-phthalimide;

n and m are each independently a whole number e.g. 0, 1, 2, 3 or 4, with n and/or m equal a positive integer such as 1 or 2 being often preferred.

In certain preferred aspects, for the radicals $R^1OOC(CX_2)_n-$ and $R^3OOC(CX_2)_m-$ of Formula I where n and m are each greater than one, preferably the first carbon of the radical directly covalently linked to the ring nitrogen has both X groups equal to hydrogen, e.g. the radicals where n and m are each two preferably have the formulae of $R^1OOC(CX_2CH_2)-$ and $R^3OOC(CX_2CH_2)_m-$ where one or more of the X groups on the beta carbon are other than hydrogen such as fluoro.

For many embodiments, preferred compounds include those where one or more X groups are hydrogen such as compounds of the following Formula IA:

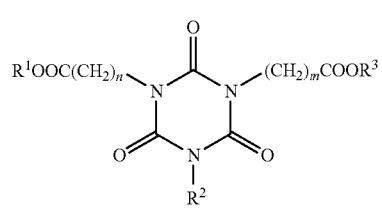

IA wherein at least two of the radicals $R^1OOC(CX_2)_n-$, $R^2-$ and $R^3OOC(CH_2)_m-$ are different acid or ester groups; and $R^1$, $R^2$ and $R^3$ are each independently hydrogen or non-hydrogen substituent such as optionally substituted alkyl (e.g. optionally substituted $C_{1-10}$ alkyl), optionally substituted alkenyl or alkynyl preferably having 2 to about 10 carbon atoms such as such as allyl, optionally substituted alkanoyl preferably having 1 to about 10 carbon atoms; optionally substituted alkoxy (including epoxy) preferably having 1 to about 10 carbon atoms such as methoxy, propoxy, butoxy; optionally substituted alkylthio preferably having 1 to about 10 carbon atoms; optionally substituted alkylsulfinyl preferably 1 to about 10 carbon atoms; optionally substituted alkylsulfonyl preferably having 1 to about 10 carbon atoms; optionally substituted carboxy preferably have 1 to about 10 carbon atoms (which includes groups such as —COOR' where R' is H or $C_{1-8}$alkyl, including esters that are substantially non-reactive with photoacid); optionally substituted alkaryl such as optionally substituted benzyl, optionally substituted carbocyclic aryl such as optionally substituted phenyl, naphthyl, acenaphthyl, or optionally substituted heteralicyclic or heteroaromatic group such as methylphthalimide, N-methyl-1,8-phthalimide;

n and m are each independently a whole number e.g. 0, 1, 2, 3 or 4, with n and/or m equal a positive integer such as 1 or 2 being often preferred.

By stating herein that at least two of the radicals $R^1OOC(CX_2)_n$—, $R^2$— and $R^3OOC(CX_2)_m$— are different acid or ester groups (or, in the case of Formula IA, at least two of the radicals $R^1OOC(CH_2)_n$—, $R^2$— and $R^3OOC(CH_2)_m$— are different acid or ester groups), it is meant that at least two radicals will have at least one atom difference. For example, if values of n and m are not equal, then the groups will be different acid or ester groups. If the groups $R^1$ and $R^3$ are not the same (e.g. $R^1$ is —$CH_3$ and $R^3$ is H), then the groups will be different acid or ester groups. If $R^2$ is an acid, and the $R^3$ is other than hydrogen, then the groups are different. In many cases, the radicals will differ by two or more atoms.

In the above Formulae I and IA, preferred $R^1$ and $R^3$ moieties include optionally substituted alkyl (which includes cycloalkyl), preferably an alkyl (which includes cycloalkyl) having 3 to 8 carbons. $R^2$ groups containing acid moieties or alkyl ester moieties also are preferred.

In certain embodiments, preferred compounds are those of Formulae I and IA above wherein at least one of $R^1$, $R^2$ and $R^3$ contain one or more halogen atoms particularly one or more fluorine atoms and/or one or more chlorine atoms such as haloalkyl and alkylaryl (such as halophenyl or halonaphthyl) e.g. —$CF_3$, >$CF_2$, —$CHF_2$, >CHF, —$CH_2F$, $C_6H_{5-x}F_x$, $C_6H_{5-x}Cl_x$, —$CCl_3$, →$CCl_2$, —$CHCl_2$, →CHCl, —$CH_2Cl$. Generally preferred are compounds of Formulae I and IA where $R^2$ has halogen-substitution.

In a yet further aspect, antireflective compositions are provided that comprises a resin as disclosed herein.

The group $R^2$ of the above Formulae I and IA can be useful to introduce various functionalities to the subsequently polymers comprising the groups, including to impart desired lithographic properties such as optical properties, etch rates, thermal properties, solubility in coating solvents and coating properties over different substrate surfaces. The group $R^2$ of the above Formula I also can influence the polymerization process for obtaining a more linear and higher molecular coating polymer compositions.

Preferred resins of the invention may be prepared using one or more compounds of Formulae I and II as reagents. Particularly preferred resins may include a tethered (covalently linked) crosslinker component that provides hardening of an applied coating layer containing the resin.

As discussed above, underlying coating compositions are also provided which preferably may include one or more resins as disclosed herein. Preferred additional components of an underlying composition include a crosslinking functionality or material. Preferred underlying coating compositions are formulated as organic solvent compositions for spin-on application to a desired substrate such as a microelectronic wafer.

Preferred coating compositions of the invention are crosslinked prior to treatment to modulate water contact angle. Such crosslinking includes hardening and covalent-bonding forming reactions between one or more composition components.

For antireflective applications, underlying compositions of the invention also preferably contain a component that comprises chromophore groups that can absorb undesired radiation used to expose the overcoated resist layer from reflecting back into the resist layer. Such chromophore groups may be present with other composition components such as the resin(s) or an acid generator compound, or the composition may comprise another component that may comprise such chromophore units, e.g. a small molecule (e.g. MW less than about 1000 or 500) that contains one or more chromophore moieties, such as one or more optionally substituted phenyl, optionally substituted anthracene or optionally substituted naphthyl groups.

Generally preferred chromophores for inclusion in coating composition of the invention particularly those used for antireflective applications include both single ring and multiple ring aromatic groups such as optionally substituted phenyl, optionally substituted naphthyl, optionally substituted anthracenyl, optionally substituted phenanthracenyl, optionally substituted quinolinyl, and the like. Particularly preferred chromophores may vary with the radiation employed to expose an overcoated resist layer. More specifically, for exposure of an overcoated resist at 248 nm, optionally substituted anthracene and optionally substituted naphthyl are preferred chromophores of the antireflective composition. For exposure of an overcoated resist at 193 nm, optionally substituted phenyl and optionally substituted naphthyl are particularly preferred chromophores of the antireflective composition. Preferably, such chromophore groups are linked (e.g. pendant groups) to a resin component of the antireflective composition.

As discussed above, coating compositions of the invention preferably are crosslinking compositions and contain a material that will crosslink or otherwise cure upon e.g. thermal or activating radiation treatment. Typically, the composition will contain a crosslinker component, e.g. an amine-containing material such as a melamine, glycouril or benzoguanamine compound or resin.

Preferably, crosslinking compositions of the invention can be cured through thermal treatment of the composition coating layer. Suitably, the coating composition also contains an acid or more preferably an acid generator compound, particularly a thermal acid generator compound, to facilitate the crosslinking reaction.

For use as an antireflective coating composition, as well as other applications such as via-fill, preferably the composition is crosslinked prior to applying a photoresist composition layer over the composition layer.

A variety of photoresists may be used in combination (i.e. overcoated) with a coating composition of the invention. Preferred photoresists for use with the antireflective compositions of the invention are chemically-amplified resists, especially positive-acting photoresists that contain one or more photoacid generator compounds and a resin component that contains units that undergo a deblocking or cleavage reaction in the presence of photogenerated acid, such as photoacid-labile ester, acetal, ketal or ether units. Negative-acting photoresists also can be employed with coating compositions of the invention, such as resists that crosslink (i.e. cure or harden) upon exposure to activating radiation. Preferred photoresists for use with a coating composition of the invention may be imaged with relatively short-wavelength radiation, e.g. radiation having a wavelength of less than 300 nm or less than 260 nm such as 248 nm, or radiation having a wavelength of less than about 200 nm such as 193 nm.

The invention further provides methods for forming a photoresist relief image and novel articles of manufacture comprising substrates (such as a microelectronic wafer substrate) coated with a coating composition of the invention alone or in combination with a photoresist composition.

Other aspects of the invention are disclosed infra.

We now provide new organic coating compositions that are particularly useful with an overcoated photoresist layer. Preferred coating compositions of the invention may be applied by spin-coating (spin-on compositions) and formulated as a solvent composition. The coating compositions of the invention are especially useful as antireflective compositions for an overcoated photoresist and/or as planarizing or via-fill compositions for an overcoated photoresist composition coating layer.

As discussed above, in a preferred aspect, cyanurate-type compounds are provided that comprise substitution of multiple cyanurate nitrogen ring atoms by distinct (different) carboxy (e.g. —$(CX_2)_n$COOH where X and n are as defined in Formula I above) and/or carboxy ester (e.g. —$(CH_2)_n$COOR where X and n are as defined in Formula I above and R is other than hydrogen such as $C_{1-12}$alkyl) substitution. Also preferred are resins provided by reaction of such monomer compounds.

In another preferred aspect, cyanurate-type monomers are provided that comprise halo-substitution, particularly fluoro or chloro substation. Also preferred are resins provided by reaction of such monomer compounds.

Resins:

As discussed above, preferred resins include those that are formed with one or more reagents selected from Formula I above. An acidic or basic condensation reaction can be suitable. Preferably, the reagents selected from Formula I constitute at least about 5 percent of the total repeat units of the formed resin, more preferably at least about 10, 15, 20, 25, 30, 35, 40, 45, 50 or 55 percent of the total repeat units of the formed resin.

One preferred synthesis route is depicted in the following Scheme I:

Scheme I:

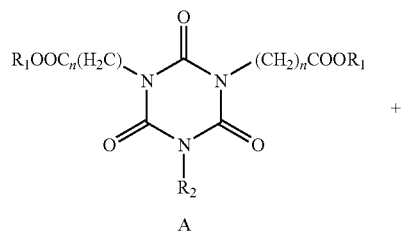

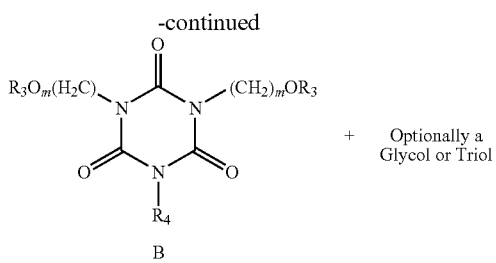

+ Optionally a Glycol or Triol

In the above Scheme I, $R_2$ and $R_4$ are the same as $R^2$ Formulae I and IA above and may be readily grafted onto the monomer compounds e.g. as exemplified in the following Scheme II. Each $R_1$ and $R_3$ in Scheme I above is independently the same as defined for $R^1$ and $R^3$ in Formula I and IA above:

Scheme II

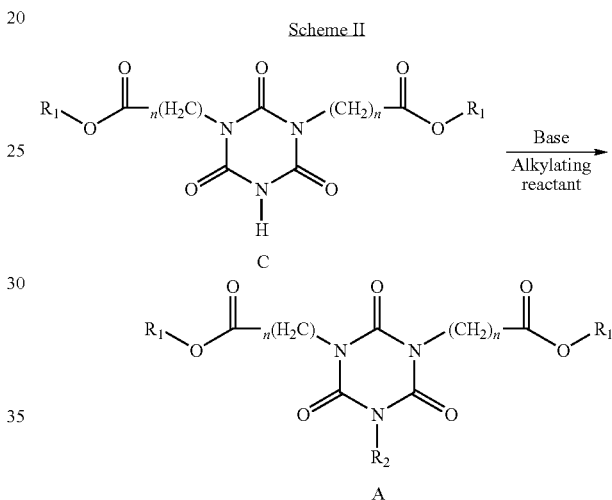

In the above Scheme II, each $R_1$ is independently a group as defined for $R^1$ in Formula I above and preferably each $R_1$ in Scheme II is independently e.g. hydrogen $C_{1-20}$alkyl preferably $C_{1-10}$alkyl, $C_{1-20}$alkoxy preferably $C_{1-10}$alkoxy, $C_{7-20}$alkylaryl, and $R_2$ in Scheme II is the same as $R^2$ in Formula I above.

Suitable polyol reagents include diols, glycerols and triols such as e.g. diols such as diol is ethylene glycol, 1,2-propylene glycol, 1,3-propylene glycol, butane diol, pentane diol, cyclobutyl diol, cyclopentyl diol, cyclohexyl diol, dimethylolcyclohexane, and triols such as glycerol, trimethylolethane, trimethylolpropane and the like.

Specifically suitable resin syntheses are also set forth in the examples which follow.

As discussed, for antireflective applications, suitably one or more of the compounds reacted to form the resin comprise a moiety that can function as a chromophore to absorb radiation employed to expose an overcoated photoresist coating layer. For example, a phthalate compound (e.g. a phthalic acid or dialkyl phthalate (i.e. di-ester such as each ester having 1-6 carbon atoms, preferably a di-methyl or ethyl phthalate) may be polymerized with an aromatic or non-aromatic polyol and optionally other reactive compounds to provide a polyester particularly useful in an antireflective composition employed with a photoresist imaged at sub-200 nm wavelengths such as 193 nm. Similarly, resins to be used in compositions with an overcoated photoresist imaged at sub-300 nm wavelengths or sub-200 nm wavelengths such as 248 nm or 193 nm, a naphthyl compound may be polymerized, such as a naphthyl compound containing one or two or more carboxyl substituents e.g. dialkyl particularly di-$C_{1-6}$alkyl naphthalenedicarboxylate. Reactive anthracene compounds also are preferred, e.g. an anthracene compound having one or more carboxy or ester groups, such as one or more methyl ester or ethyl ester groups.

The compound that contains a chromophore unit also may contain one or preferably two or more hydroxy groups and be reacted with a carboxyl-containing compound. For example, a phenyl compound or anthracene compound having one, two or more hydroxyl groups may be reacted with a carboxyl-containing compound.

Additionally, underlying coating composition that are employed for antireflective purposes may contain a material that contains chromophore units that is separate from a resin component that provides water contact angle modulation (e.g. a resin that contains photoacid-labile groups and/or base-reactive groups. For instance, the coating composition may comprise a polymeric or non-polymeric compound that contain phenyl, anthracene, naphthyl, etc. units. It is often preferred, however, that the one or more resins that provide water contact angle modulation also chromophore moieties.

Preferably resins of underlying coating compositions of the invention will have a weight average molecular weight (Mw) of about 1,000 to about 10,000,000 daltons, more typically about 2,000 to about 100,000 daltons, and a number average molecular weight (Mn) of about 500 to about 1,000,000 daltons. Molecular weights (either Mw or Mn) of the polymers of the invention are suitably determined by gel permeation chromatography.

As mentioned, preferred underlying coating compositions of the invention can be crosslinked, e.g. by thermal and/or radiation treatment. For example, preferred underlying coating compositions of the invention may contain a separate crosslinker component that can crosslink with one or more other components of the coating composition. Generally preferred crosslinking coating compositions comprise a separate crosslinker component. Particularly preferred coating compositions of the invention contain as separate components: a resin, a crosslinker, and an acid source such as a thermal acid generator compound. Thermal-induced crosslinking of the coating composition by activation of the thermal acid generator is generally preferred.

Suitable thermal acid generator compounds for use in a coating composition include ionic or substantially neutral thermal acid generators, e.g. an ammonium arenesulfonate salt, for catalyzing or promoting crosslinking during curing of an antireflective composition coating layer. Typically one or more thermal acid generators are present in an coating composition in a concentration from about 0.1 to 10 percent by weight of the total of the dry components of the composition (all components except solvent carrier), more preferably about 2 percent by weight of the total dry components.

Preferred crosslinking-type coating compositions of the invention also contain a crosslinker component. A variety of crosslinkers may be employed, including those crosslinkers disclosed in Shipley European Application 542008 incorporated herein by reference. For example, suitable coating composition crosslinkers include amine-based crosslinkers such as melamine materials, including melamine resins such as manufactured by Cytec Industries and sold under the tradename of Cymel 300, 301, 303, 350, 370, 380, 1116 and 1130. Glycolurils are particularly preferred including glycolurils available from Cytec Industries. Benzoquanamines and urea-based materials also will be suitable including resins such as the benzoquanamine resins available from Cytec Industries under the name Cymel 1123 and 1125, and urea resins available from Cytec Industries under the names of Powderlink 1174 and 1196. In addition to being commercially available, such amine-based resins may be prepared e.g. by the reaction of acrylamide or methacrylamide copolymers with formaldehyde in an alcohol-containing solution, or alternatively by the copolymerization of N-alkoxymethyl acrylamide or methacrylamide with other suitable monomers.

A crosslinker component of a coating composition of the invention in general is present in an amount of between about 5 and 50 weight percent of total solids (all components except solvent carrier) of the antireflective composition, more typically in an amount of about 7 to 25 weight percent total solids.

Coating compositions of the invention, particularly for reflection control applications, also may contain additional dye compounds that absorb radiation used to expose an overcoated photoresist layer. Other optional additives include surface leveling agents, for example, the leveling agent available under the tradename Silwet 7604, or the surfactant FC 171 or FC 431 available from the 3M Company.

Underlying coating compositions of the invention also may contain other materials such as a photoacid generator, including a photoacid generator as discussed for use with an overcoated photoresist composition. See U.S. Pat. No. 6,261,743 for a discussion of such use of a photoacid generator in an antireflective composition.

To make a liquid coating composition of the invention, the components of the coating composition are dissolved in a suitable solvent such as, for example, one or more oxyisobutyric acid esters particularly methyl-2-hydroxyisobutyrate as discussed above, ethyl lactate or one or more of the glycol ethers such as 2-methoxyethyl ether (diglyme), ethylene glycol monomethyl ether, and propylene glycol monomethyl ether; solvents that have both ether and hydroxy moieties such as methoxy butanol, ethoxy butanol, methoxy propanol, and ethoxy propanol; methyl 2-hydroxyisobutyrate; esters such as methyl cellosolve acetate, ethyl cellosolve acetate, propylene glycol monomethyl ether acetate, dipropylene glycol monomethyl ether acetate and other solvents such as dibasic esters, propylene carbonate and gamma-butyro lactone. The concentration of the dry components in the solvent will depend on several factors such as the method of application. In general, the solids content of an underlying coating composition varies from about 0.5 to 20 weight percent of the total weight of the coating composition, preferably the solids content varies from about 0.5 to 10 weight of the coating composition.

Exemplary Photoresist Systems

A variety of photoresist compositions can be employed with coating compositions of the invention, including positive-acting and negative-acting photoacid-generating compositions. Photoresists used with antireflective compositions of the invention typically comprise a resin binder and a photoactive component, typically a photoacid generator compound. Preferably the photoresist resin binder has functional groups that impart alkaline aqueous developability to the imaged resist composition.

As discussed above, particularly preferred photoresists for use with underlying coating compositions of the invention are chemically-amplified resists, particularly positive-acting chemically-amplified resist compositions, where the photoactivated acid in the resist layer induces a deprotection-type reaction of one or more composition components to thereby provide solubility differentials between exposed and unexposed regions of the resist coating layer. A number of chemically-amplified resist compositions have been described, e.g., in U.S. Pat. Nos. 4,968,581; 4,883,740; 4,810,613; 4,491,628 and 5,492,793. Coating compositions of the invention are particularly suitably used with positive chemically-amplified photoresists that have acetal groups that undergo deblocking in the presence of a photoacid. Such acetal-based resists have been described in e.g. U.S. Pat. Nos. 5,929,176 and 6,090,526.

Underlying coating compositions of the invention also may be used with other positive resists, including those that contain resin binders that comprise polar functional groups such as hydroxyl or carboxylate and the resin binder is used in a resist composition in an amount sufficient to render the resist developable with an aqueous alkaline solution. Generally preferred resist resin binders are phenolic resins including phenol aldehyde condensates known in the art as novolak resins, homo and copolymers or alkenyl phenols and homo and copolymers of N-hydroxyphenyl-maleimides.

Preferred positive-acting photoresists for use with an underlying coating composition of the invention contains an imaging-effective amount of photoacid generator compounds and one or more resins that are selected from the group of:

1) a phenolic resin that contains acid-labile groups that can provide a chemically amplified positive resist particularly suitable for imaging at 248 nm. Particularly preferred resins of this class include: i) polymers that contain polymerized units of a vinyl phenol and an alkyl acrylate, where the polymerized alkyl acrylate units can undergo a deblocking reaction in the presence of photoacid. Exemplary alkyl acrylates that can undergo a photoacid-induced deblocking reaction include e.g. t-butyl acrylate, t-butyl methacrylate, methyladamantyl acrylate, methyl adamantyl methacrylate, and other non-cyclic alkyl and alicyclic acrylates that can undergo a photoacid-induced reaction, such as polymers in U.S. Pat. Nos. 6,042,997 and 5,492,793; ii) polymers that contain polymerized units of a vinyl phenol, an optionally substituted vinyl phenyl (e.g. styrene) that does not contain a hydroxy or carboxy ring substituent, and an alkyl acrylate such as those deblocking groups described with polymers i) above, such as polymers described in U.S. Pat. No. 6,042,997; and iii) polymers that contain repeat units that comprise an acetal or ketal moiety that will react with photoacid, and optionally aromatic repeat units such as phenyl or phenolic groups; such polymers have been described in U.S. Pat. Nos. 5,929,176 and 6,090,526.

2) a resin that is substantially or completely free of phenyl or other aromatic groups that can provide a chemically amplified positive resist particularly suitable for imaging at sub-200 nm wavelengths such as 193 nm. Particularly preferred resins of this class include: i) polymers that contain polymerized units of a non-aromatic cyclic olefin (endocyclic double bond) such as an optionally substituted norbornene, such as polymers described in U.S. Pat. Nos. 5,843,624, and 6,048,664; ii) polymers that contain alkyl acrylate units such as e.g. t-butyl acrylate, t-butyl methacrylate, methyladamantyl acrylate, methyl adamantyl methacrylate, and other non-cyclic alkyl and alicyclic acrylates; such polymers have been described in U.S. Pat. No. 6,057,083; European Published Applications EP01008913A1 and EP00930542A1; and U.S. pending patent application Ser. No. 09/143,462; iii) polymers that contain polymerized anhydride units, particularly polymerized maleic anhydride and/or itaconic anhydride units, such as disclosed in European Published Application EP01008913A1 and U.S. Pat. No. 6,048,662.

3) a resin that contains repeat units that contain a hetero atom, particularly oxygen and/or sulfur (but other than an anhydride, i.e. the unit does not contain a keto ring atom), and preferable are substantially or completely free of any aromatic units. Preferably, the heteroalicyclic unit is fused to the resin backbone, and further preferred is where the resin comprises a fused carbon alicyclic unit such as provided by polymerization of a norborene group and/or an anhydride unit such as provided by polymerization of a maleic anhydride or itaconic anhydride. Such resins are disclosed in PCT/US01/14914 and U.S. application Ser. No. 09/567,634.

4) a resin that contains fluorine substitution (fluoropolymer), e.g. as may be provided by polymerization of tetrafluoroethylene, a fluorinated aromatic group such as fluoro-styrene compound, and the like. Examples of such resins are disclosed e.g. in PCT/US99/21912.

Suitable photoacid generators to employ in a positive or negative acting photoresist overcoated over a coating composition of the invention include imidosulfonates such as compounds of the following formula:

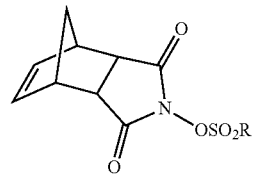

wherein R is camphor, adamantane, alkyl (e.g. $C_{1-12}$ alkyl) and fluoroalkyl such as fluoro($C_{1-18}$alkyl) e.g. $RCF_2$— where R is optionally substituted adamantyl.

Also preferred is a triphenyl sulfonium PAG, complexed with anions such as the sulfonate anions mentioned above, particularly a perfluoroalkyl sulfonate such as perfluorobutane sulfonate.

Other known PAGS also may be employed in the resists of the invention. Particularly for 193 nm imaging, generally preferred are PAGS that do not contain aromatic groups, such as the above-mentioned imidosulfonates, in order to provide enhanced transparency.

Other suitable photoacid generators for use in compositions of the invention include for example: onium salts, for example, triphenylsulfonium trifluoromethanesulfonate, (p-tert-butoxyphenyl)diphenylsulfonium trifluoromethanesulfonate, tris(p-tert-butoxyphenyl)sulfonium trifluoromethanesulfonate, triphenylsulfonium p-toluenesulfonate; nitrobenzyl derivatives, for example, 2-nitrobenzyl p-toluenesulfonate, 2,6-dinitrobenzyl p-toluenesulfonate, and 2,4-dinitrobenzyl p-toluenesulfonate; sulfonic acid esters, for example, 1,2,3-tris(methanesulfonyloxy)benzene, 1,2,3-tris(trifluoromethanesulfonyloxy)benzene, and 1,2,3-tris(p-toluenesulfonyloxy)benzene, diazomethane derivatives, for example, bis(benzenesulfonyl)diazomethane, bis(p-toluenesulfonyl)diazomethane; glyoxime derivatives, for example, bis-O-(p-toluenensulfonyl)-α-dimethylglyoxime, and bis-O-(n-butanesulfonyl)-α-dimethylglyoxime; sulfonic acid ester derivatives of an N-hydroxyimide compound, for example, N-hydroxysuccinimide methanesulfonic acid ester, N-hydroxysuccinimide trifluoromethanesulfonic acid ester; and halogen-containing triazine compounds, for example, 2-(4-methoxyphenyl)-4,6-bis(trichloromethyl)-1,3,5-triazine, and 2-(4-methoxynaphthyl)-4,6-bis(trichloromethyl)-1,3,5-triazine. One or more of such PAGs can be used.

A preferred optional additive of resists of the invention is an added base, particularly tetrabutylammonium hydroxide (TBAH), or tetrabutylammonium lactate, which can enhance resolution of a developed resist relief image. For resists imaged at 193 nm, a preferred added base is a lactate salt of tetrabutylammonium hydroxide as well as various other amines such as triisopropanol, diazabicyclo undecene or diazabicyclononene. The added base is suitably used in relatively small amounts, e.g. about 0.03 to 5 percent by weight relative to the total solids.

Preferred negative-acting resist compositions for use with an overcoated coating composition of the invention comprise a mixture of materials that will cure, crosslink or harden upon exposure to acid, and a photoacid generator.

Particularly preferred negative-acting resist compositions comprise a resin binder such as a phenolic resin, a crosslinker component and a photoactive component of the invention. Such compositions and the use thereof have been disclosed in European Patent Applications 0164248 and 0232972 and in U.S. Pat. No. 5,128,232 to Thackeray et al. Preferred phenolic resins for use as the resin binder component include novolaks and poly(vinylphenol)s such as those discussed above. Preferred crosslinkers include amine-based materials, including melamine, glycolurils, benzoguanamine-based materials and urea-based materials. Melamine-formaldehyde resins are generally most preferred. Such crosslinkers are commercially available, e.g. the melamine resins sold by Cytec Industries under the trade names Cymel 300, 301 and 303. Glycoluril resins are sold by Cytec Industries under trade names Cymel 1170, 1171, 1172, Powderlink 1174, and benzoguanamine resins are sold under the trade names of Cymel 1123 and 1125.

Photoresists of the invention also may contain other optional materials. For example, other optional additives include anti-striation agents, plasticizers, speed enhancers, dissolution inhibitors, etc. Such optional additives typically will be present in minor concentrations in a photoresist composition except for fillers and dyes which may be present in relatively large concentrations, e.g., in amounts of from about 5 to 30 percent by weight of the total weight of a resist's dry components.

Lithographic Processing

In use, a coating composition of the invention is applied as a coating layer to a substrate by any of a variety of methods such as spin coating. The coating composition in general is applied on a substrate with a dried layer thickness of between about 0.02 and 0.5 µm, preferably a dried layer thickness of between about 0.04 and 0.20 µm. The substrate is suitably any substrate used in processes involving photoresists. For example, the substrate can be silicon, silicon dioxide or aluminum-aluminum oxide microelectronic wafers. Gallium arsenide, silicon carbide, ceramic, quartz or copper substrates may also be employed. Substrates for liquid crystal display or other flat panel display applications are also suitably employed, for example glass substrates, indium tin oxide coated substrates and the like. Substrates for optical and optical-electronic devices (e.g. waveguides) also can be employed.

Preferably the applied coating layer is cured before a photoresist composition is applied over the underlying coating composition. Cure conditions will vary with the components of the underlying coating composition. Particularly the cure temperature will depend on the specific acid or acid (thermal) generator that is employed in the coating composition. Typical cure conditions are from about 80° C. to 225° C. for about 0.5 to 5 minutes. Cure conditions preferably render the coating composition coating layer substantially insoluble to the photoresist solvent as well as an alkaline aqueous developer solution.

After such curing, a photoresist is applied above the surface of the applied coating composition. As with application of the bottom coating composition layer(s), the overcoated photoresist can be applied by any standard means such as by spinning, dipping, meniscus or roller coating. Following application, the photoresist coating layer is typically dried by heating to remove solvent preferably until the resist layer is tack free. Optimally, essentially no intermixing of the bottom composition layer and overcoated photoresist layer should occur.

The resist layer is then imaged with activating radiation through a mask in a conventional manner. The exposure energy is sufficient to effectively activate the photoactive component of the resist system to produce a patterned image in the resist coating layer. Typically, the exposure energy ranges from about 3 to 300 mJ/cm$^2$ and depending in part upon the exposure tool and the particular resist and resist processing that is employed. The exposed resist layer may be subjected to a post-exposure bake if desired to create or enhance solubility differences between exposed and unexposed regions of a coating layer. For example, negative acid-hardening photoresists typically require post-exposure heating to induce the acid-promoted crosslinking reaction, and many chemically amplified positive-acting resists require post-exposure heating to induce an acid-promoted deprotection reaction. Typically post-exposure bake conditions include temperatures of about 50° C. or greater, more specifically a temperature in the range of from about 50° C. to about 160° C.

The photoresist layer also may be exposed in an immersion lithography system, i.e. where the space between the exposure tool (particularly the projection lens) and the photoresist coated substrate is occupied by an immersion fluid, such as water or water mixed with one or more additives such as cesium sulfate which can provide a fluid of enhanced refractive index. Preferably the immersion fluid (e.g., water) has been treated to avoid bubbles, e.g. water can be degassed to avoid nanobubbles.

References herein to "immersion exposing" or other similar term indicates that exposure is conducted with such a fluid layer (e.g. water or water with additives) interposed between an exposure tool and the coated photoresist composition layer.

The exposed resist coating layer is then developed, preferably with an aqueous based developer such as an alkali exemplified by tetra butyl ammonium hydroxide, sodium hydroxide, potassium hydroxide, sodium carbonate, sodium bicarbonate, sodium silicate, sodium metasilicate, aqueous ammonia or the like. Alternatively, organic developers can be used. In general, development is in accordance with art recognized procedures. Following development, a final bake of an acid-hardening photoresist is often employed at temperatures of from about 100° C. to about 150° C. for several minutes to further cure the developed exposed coating layer areas.

The developed substrate may then be selectively processed on those substrate areas bared of photoresist, for example, chemically etching or plating substrate areas bared of photoresist in accordance with procedures well known in the art. Suitable etchants include a hydrofluoric acid etching solution and a plasma gas etch such as an oxygen plasma etch. A plasma gas etch removes the underlying coating layer.

A plasma etch conducted by the following protocol: a coated substrate (e.g., substrate coated with an underlying coating composition and resist in accordance with the invention) is placed in a plasma etch chamber (e.g., Mark II Oxide Etch Chamber) at 25 mT pressure, top power of 600 watts, 33 CHF$_3$ (Sccm), 7O$_2$ (Sccm) and 80 Ar (Sccm).

The following non-limiting examples are illustrative of the invention. All documents mentioned herein are incorporated herein by reference.

Example 1

General Synthesis Procedure to Prepare Monomers of Formula I According to Scheme II Above Butyl bis(CarboxyEthyl)IsoCyanuric acid) esters, 200 g, is dissolved in 525 g THF at room temperature. The homogenous solution is cooled to 0° C. in an ice bath followed by the addition of 125.14 g benzyl bromide. When a clear solution is obtained, 98.7 g of 1,8-diazabicyclo[5.4.0]-undec-7-ene, DBU, is slowly added to the reaction mixture. On complete addition of DBU, the contents are stirred overnight at room temperature to obtain thick white precipitate of the salt. The precipitates are filtered and the organic phase diluted by addition of 500 ml ethyl acetate. The combined organic phase is washed with 0.1 N HCl followed by water washes to obtain a neutral pH on the aqueous phase. The organic phase is dried with sodium sulfate followed by vacuum drying to yield about 210 g of a viscous oil. The purity of the monomer was determined using $^1$H NMR, $^{13}$C NMR and HPLC to be about >99%.

Example 2 to 12 are Other Useful Monomers Prepared According to the General Procedure of Example 1

In the following Table, the group $R_1$ designates the $R_1$ substituent of a compound C as set forth in Scheme II above, and $R_2$ designates the $R_2$ substituent of a compound A as set forth in Scheme II above.

TABLE 1

| Example | $R_1$ | $R_2$ |
|---|---|---|
| 2 | —CH$_2$CH$_3$ | —CH$_3$ |
| 3 | —CH$_2$CH$_3$ | —CH$_2$I |
| 4 | —CH$_2$CH$_3$ | —CH$_2$CHOHCH$_3$ |
| 5 | —CH$_2$CH$_2$CH$_2$CH$_3$ | —CH$_2$CH=CH$_2$ |
| 6 | —CH$_2$CH$_2$CH$_2$CH$_3$ | —H$_2$C—C$_6$H$_5$ |
| 7 | —CH$_2$CH$_2$CH$_2$CH$_3$ | —H$_2$C—C$_6$F$_5$ |
| 8 | —CH$_2$CH$_2$CH$_2$CH$_3$ | —CH$_2$COOC(CH3)$_3$ |
| 9 | —CH$_2$CH$_2$CH$_2$CH$_3$ | —CH$_2$COOCH$_2$-cyclohexyl |
| 10 | —CH$_2$CH$_2$CH$_2$CH$_3$ | —CH$_2$COOCH$_2$-phenyl |
| 11 | —CH$_2$CH$_2$CH$_2$CH$_3$ | —CH$_2$COOCH$_2$-(4-F-phenyl) |
| 12 | —CH$_2$CH$_2$CH$_2$CH$_3$ | —CH$_2$COOCH$_2$-(pentafluorophenyl) |

Example 13

Alkylation of Butyl Bis(Carboxyethyl)Isocyanuric Acid) Esters with Epichlorohydrin Butyl bis(CarboxyEthyl)IsoCyanuric acid) esters, 30 g, Sodium Carbonate, 8.16 g, Benzyl Trimethyl Ammonium Chloride (3.85 mmol), Epichlorohydrin, 8.5 g, and 100 mL of Dioxane were charged into a 250 mL round bottom flask equipped with a magnetic stirrer and overhead condenser. The flask was placed in an oil bath set at 90° C. and allowed to stir for 12 hours. The reaction contents were allowed to cool and diluted with 200 mL of distilled water. The contents were then extracted into Ethyl acetate (300 mL) and washed twice with 200 mL portions of water, dried over sodium sulfate and followed by solvent removed on a rotary evaporator. The product was further dried under vacuum to afford a viscous oil (30 g, 89% yields).

Example 14

To a 500 ml, 3 neck round bottom flask was charged with 100 g of monomer B ($R_3$ is H), 133.18 g of monomer of Example 5, 2.25 g of para-toluenesulfonic acid, and 164 g of anisole. The flask was heated to 140°-160° C. while the contents were vigorously stirred. Butanol along with anisole was slowly distilled out of the reaction flask. 145 g of distillate was collected over a 6 hr time period. The viscous polymer solution was then diluted with 509 g of methyl-2-hydroxy isobutyrate. A 100 g sample of this solution was added to 1000 mL isopropanol to precipitate to polymer. The resulting precipitate was collected on a filter, partially air dried followed by vacuum oven drying to yield a white powders whose characteristics are presented in Table 2.

The procedure according to Example 14 was used to prepare polymers of Examples 15 to 22. Monomer B has the structure of compound B in Scheme I above with $R_3$=H, $R_4$=(CH$_2$)$_2$OH; references throughout these examples to Monomer B indicates the structure of compound B in Scheme I above such $R_3$ and $R_4$ groups, this Monomer B also known as THEIC. The characteristics of the polymers, as well as those of Example 14 are presented in Table 2. In Table 2, references to Monomer A refer to a structure A as depicted in Scheme II above.

TABLE 2

| Polymer Example | Monomer A of Example | Monomer A/B ratio | Mw | PD | $n_{193}$ | $k_{193}$ |
|---|---|---|---|---|---|---|
| 14 | 5 | 45/55 | 8160 | 1.88 | 1.997 | 0.32 |
| 15 | 2 | 50/60 | 2200 | ::::: | 1.987 | 0.315 |
| 16 | 6 | 50/50 | 2130 | 1.88 | 1.988 | 0.512 |
| 17 | 7 | 50/50 | 2650 | 1.48 | 1.965 | 0.323 |
| 18 | 8 | 50/50 | 6800 | 2.71 | 1.947 | 0.26 |

TABLE 2-continued

| Polymer Example | Monomer A of Example | Monomer A/B ratio | Mw | PD | $n_{193}$ | $k_{193}$ |
|---|---|---|---|---|---|---|
| 19 | 9 | 50/50 | 20780 | 3.77 | 1.927 | 0.244 |
| 20 | 11 | 50/50 | 28000 | ::::: | 2.015 | 0.398 |
| 21 | 12 | 50/50 | 3920 | 1.48 | 1.965 | 0.323 |
| 22 | 4 | 50/50 | 5000 | 1.95 | 1.957 | 0.303 |

Example 23

Using the procedure according to Example 14 a ter-polymer was prepared comprising of monomer A of Example 8, monomer B ($R_3$=H) at a feed ratio of 1:1 in excess 1,2-propanediol. Thus the condensation produced a polymer with Mw of 7460, PD of 2.5, $n_{193}$ of 1.926 and $k_{193}$ of 0.24.

Example 24

Anti-Reflective Polymer Comprising of Tri-Acid and Tri-Alcohol

To a 1000 ml, 3 neck round bottom flask was charged with 304 g of tris(2-hydroxyethyl)isocyanurate, 201.0 g of tris(2-carboxyethyl)isocyanurae, 5.39 g of para-toluene sulfonic acid mono-hydrae, 201.1 g of n-butanol, and 342 g of anisole. The flask was heated to 140°-160° C. and the contents were vigorously stirred. Butanol along with anisole was slowly distilled out of the reaction flask. Polymers were varying Mw were synthesized by controlling the amount of the distillate. The polymer solution was then diluted with 1587 g of methyl 2-hydroxyisobutyrate. The resulting solution was neutralized with triethyl amine and the product precipitation into a 10 fold volume solution of isopropyl alcohol/methyl t-butyl ether (50/50). The polymer was collected and dried under vacuum at 40° C.-60° C. overnight. The $GPC_{(THF)}$ Mw was 4623 with a polydispersity of 1.68 and with $n_{193}$ of 1.926 and $k_{193}$ of 0.24

In order to reduce sublimation, a crosslinker such as tetra methoxy methyl glycouril is covalently attached to the anti-reflective polymer.

Example 25

About 700 g of polymer solution from Example 14 was heated at 50° C. followed by the addition of 140 g methyl-2-hydroxyisobutyrate, and 35 g of tetramethoxymethyl glycoluril, The contents were stirred for 3 hours at 50° C. The reaction contents were then cooled to ambient temperature and neutralized with triethyl amine. Precipitation was carried out of 60/40 isopropanol/heptane (10 fold excess). The precipitates were washed with heptane and vacuum dried overnight to provide a polymer of the above structure. The resulting polymer Mw was 22175, PD of 6.18, $n_{193}$ of 1.993 and $k_{193}$ of 0.32. Using $C^{13}$ NMR was estimated that about 13.5 weight percent cross-linker was attached to the polymer.

Examples 26 and 27 are Representative of Anti-Reflecting Coating Compositions of the Invention Example 26

An anti-reflective casting solution comprising of 3.237 g of polymer from Example 19, 5.768 g of tetramethoxymethyl glycoluril, 0.371 g solution of ammoniated para-toluene sulfonic acid and 490.624 g of methyl-2-hydroxyisobutyrate was filtered through a 0.2µ Teflon filter and spin cast at over silicon wafer. The film was baked at 205° C. for 60 seconds, the thickness measured and than covered with a puddle of PGMEA for 60 seconds. After spun dry the film thickness was measured again. No significant thickness loss or gain was detected. The lack of film thickness loss or gain was also observed when a new film, processed in the same manner, was covered with MF26A developer for 60 seconds. These tests indicate that the cured films are highly cross-linked and unaffected by the solvent or developer.

Example 27

It can be desirable to blend anti-reflective polymer compositions of the invention to optimize coating and optical properties demanded by the application. Thus a solution comprising of 1.913 g of polymer of Example 19, 1.913 g of polymer of Example 25, 4.29 g of tetramethoxymethyl glycoluril, 0.371 g solution of ammoniated para-toluene sulfonic acid and 490.624 g of methyl-2-hydroxyisobutyrate was filtered through a 0.2µ Teflon filter and spin cast at over silicon wafer. Following the bake and strip test procedures used in Example 26 the films were found unaffected by PGMEA (propylene glycol methyl ether acetate) and the 0.26 N aqueous alkaline developer.

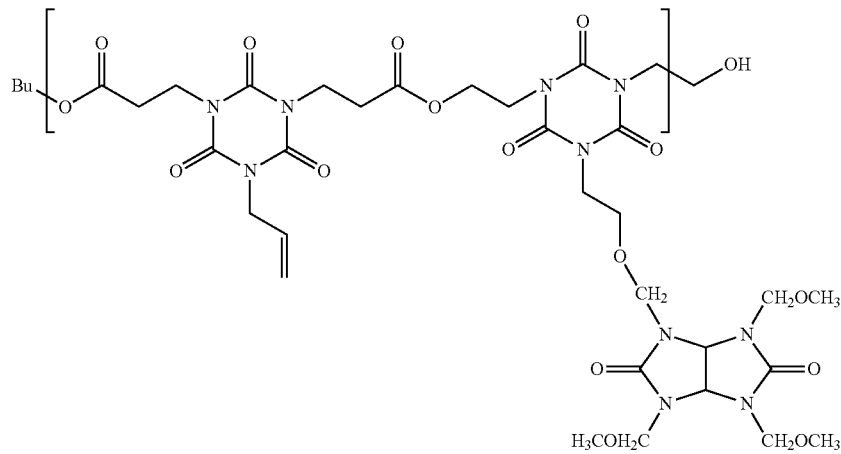

Example 28

Synthesis and Characteristics of Polymer II

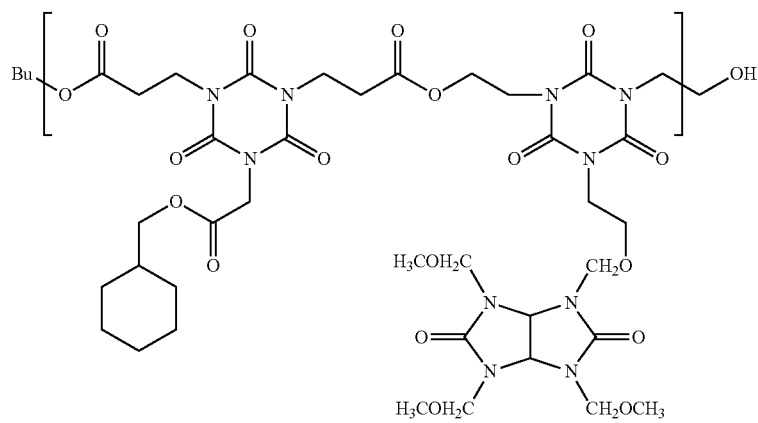

Polymer II 500 ml, 3 neck round bottom flask was charged with THEIC, 70 g (0.268 mol), Butyl-BCEIC-tBu acetate, 133.86 g (0.0.268 mol), cyclohexyl methanol, 30.60 g (0.268 mol), p-TSA 1.99 g (1 wt % of total monomers), and anisole, 142.7 g. The flask was heated to 140°-160° C. and the contents were vigorously stirred. n-Butanol along with anisole was slowly distilled out of the reaction flask. Polymer Mw range is maintained by controlling the amount of the distillate. The polymer reaction solution was then diluted with methyl-2-hydroxy isobutyrate, 650 g. The resulting solution was heated to 50° C. followed by the addition of 45.5 g tetra methoxy methyl glycouril and an additional 187 g of methyl-2-hydroxy isobutyrate. The contents were gently stirred for 3 hrs at this temperature. After three hours the reaction mixture was neutralized with triethyl amine and the polymer precipitated into 10 volumes of isopropyl alcohol/Methyl t-butyl ether (50/50). The polymer was dried in vacuum oven at 40° C.-60° C. and then characterized by GPC, $C^{13}$ NMR and ollepsometry (WVASE32 ollipsometer). The polymer showed Mw of about 16,000 Daltons, about 23% pendant glycoluril group, and $n_{193}$ of 1.93 and $k_{193}$ of 0.27. The polymer self crosslinking characteristic was tested following the procedure outlined in Example 26. No significant film thickness loss was observed when the cured polymer film was covered with PGMEA and 0.26N developer.

Example 29

Synthesis of C-Glycerol-Decanediol Polymer

Monomer C (Compound C of Scheme II above where $R_1$ is H) (200 g, 45 mol %), glycerol (60 g, 40 mol %) and 1,2-decanediol (42.5 g, 15 mol %) are charged in a 1000 ml 3 neck round bottom flask followed by the addition of 1 weight % p-TSA and anisole. The contents are shaken vigorously at 145° C. for 5-7 hrs to collect about 35 g-45 g distillate. The reaction is quenched by lowering down the reaction temperature to 80° C. and followed by the addition of THF. Residual monomer C is filtered and the filtrate was precipitated out of methyl-t-butyl ether/isopropanol (50/50 v/v) mix to yield a white powder which was dried in the vacuum oven under heat. The polymer could be precipitated from a variety of other solvents like heptane, di-isopropyl ether etc.

The polymer was subjected to various analytical tests.

$^{13}$C NMR reveals a composition consisting of 54% monomer C ($R_1$ is H), 43% glycerol and 3% 1,2-decanediol. Optical properties: $n_{193}$: 1.949; $k_{193}$: 0.192

Other polymers with varying composition can be synthesized by increasing or decreasing the charge amounts of the diol monomer. Polymer composition can also be varied to an extent by fractionation in different precipitation solvent mixtures.

For example the above polymer was enriched in diol content when precipitated from a solvent mixture of different polarity to give a new polymer composition comprising of 48% monomer. C (Compound C of Scheme II above where $R_1$ is H), 47% glycerol and 5.5% decanediol as determined by $^{13}$C NMR.

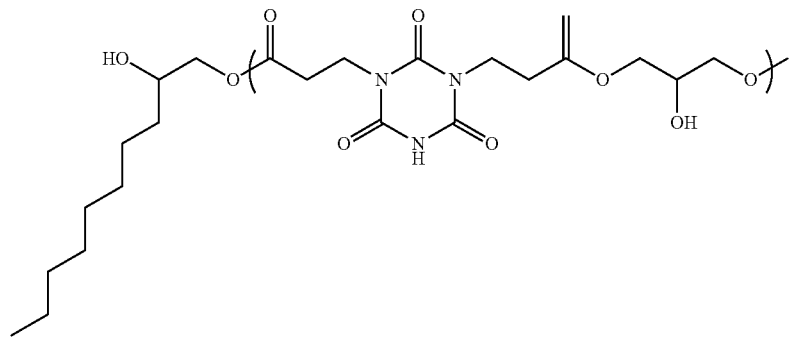

Example 30

Incorporation of Hydrophobic Component within the Polymer Chain

Without being bound by any theory, it is believed that because of steric factors the incorporation of a large hydrophobic monomer such as 1,2-decanediol occurs primarily at the end of the polymer chain. For improved distribution of the hydrophobic component within the polymer chain it is desirable to use a monomer where the hydrophobic component is further away from the reactive polymerizing groups.

Condensation of monomer $C_1$ (Compound C of Scheme II above where $R_1$ is Butyl, $R_2$ is cyclohexylethyl) with monomer C ($R_1$ and $R_2$ are H) and glycerol Monomer $C_1$ is prepared according to Scheme II

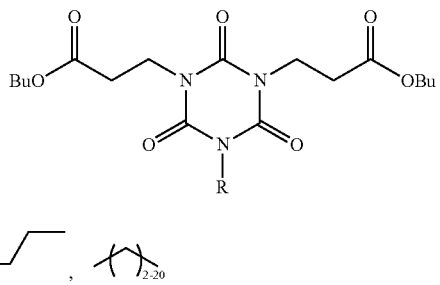

Polymer synthesis is carried out according to Example 14 above.

An exemplary polymer structure is as follows.

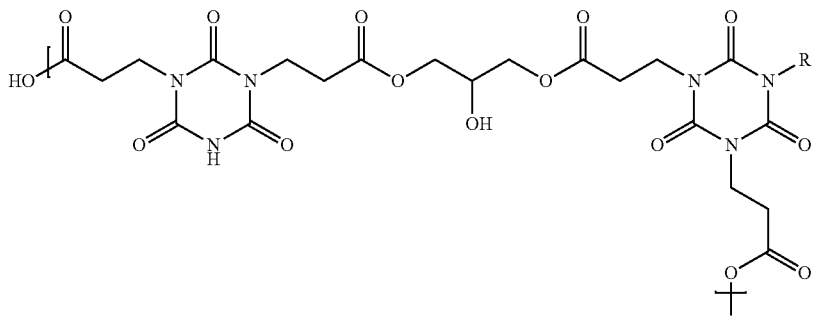

The hydrophobic component can be incorporated in the polymer by using Monomer $C_1$ ($R_1$ is Butyl, $R_2$ is cyclohexylethyl), Monomer C($R_1$ and $R_2$ is H) and glycerol or other polyols.

Scheme III

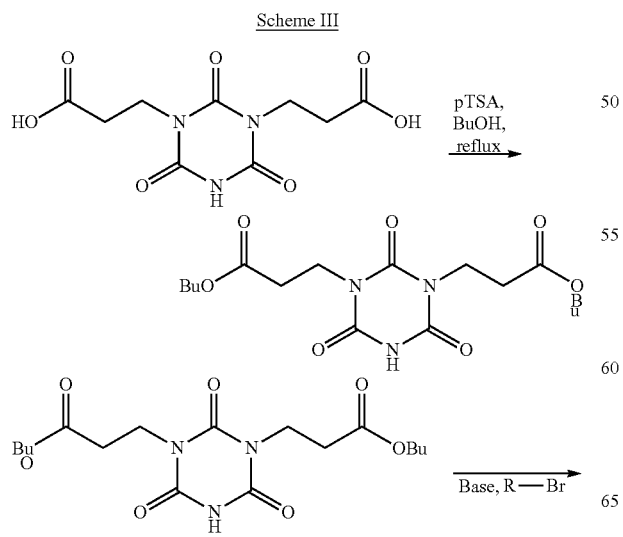

What is claimed is:

1. A cyanuarate compound corresponding to the following Formula I:

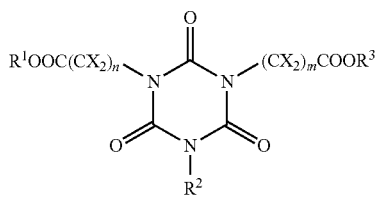

wherein at least two of the radicals $R^1OOC(CX_2)_n$—, $R^2$— and $R^3OOC(CX_2)_n$— are different acid or ester groups; and $R^1$, $R^2$ and $R^3$ and each X are each independently hydrogen or non-hydrogen substituents; and n and m the same or different and are each a whole number, and wherein the compound has halogen substitution.

2. A cyanuarate compound of claim 1 wherein the compound corresponds to the following Formula IA:

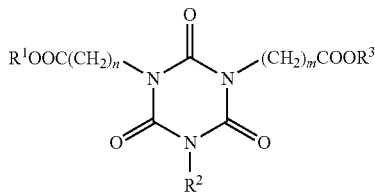

IA wherein at least two of the radicals $R^1OOC(CH_2)_n-$, $R^2-$ and $R^3OOC(CH_2)_n-$ are different acid or ester groups; and $R^1$, $R^2$ and $R^3$ are each independently hydrogen or non-hydrogen substituents; and n and m the same or different and are each a whole number.

3. A compound of claim 1 wherein the compound has fluorine substitution.

4. An antireflective composition for use with an overcoated photoresist composition, the antireflective composition comprising a resin that comprises a compound of claim 1.

5. A coated substrate comprising:
 a layer of an antireflective composition of claim 4;
 a photoresist layer over the coating composition layer.

6. A method of forming a photoresist relief image, comprising:
 applying an antireflective coating composition of claim 4 on a substrate;
 applying a photoresist composition above the coating composition layer; and
 exposing and developing the photoresist layer to provide a resist relief image.

7. The method of claim 6 wherein the antireflective composition is crosslinked prior to applying the photoresist composition.

8. An antireflective composition for use with an overcoated photoresist composition, the antireflective composition comprising a resin that comprises a compound of claim 3.

9. A method of forming a photoresist relief image, comprising:
 applying an antireflective coating composition of claim 8 on a substrate;
 applying a photoresist composition above the coating composition layer; and
 exposing and developing the photoresist layer to provide a resist relief image.

10. The method of claim 9 wherein the antireflective composition is crosslinked prior to applying the photoresist composition.

\* \* \* \* \*